United States Patent [19]
Heath

[11] 3,954,920
[45] May 4, 1976

[54] GAS HUMIDIFICATION SYSTEM

[75] Inventor: Walter I. Heath, Chicago, Ill.

[73] Assignee: Parkland International Inc., Melrose Park, Ill.

[22] Filed: Apr. 7, 1975

[21] Appl. No.: 565,537

Related U.S. Application Data
[63] Continuation of Ser. No. 394,324, Sept. 4, 1973, abandoned.

[52] U.S. Cl. ............................. 261/104; 128/192; 261/142; 261/154; 261/DIG. 65
[51] Int. Cl.² .................... A61M 15/00; B01F 3/04
[58] Field of Search ............... 261/95, 99, 104, 107, 261/142, 152–154, DIG. 65; 128/185, 186, 188, 192, 212

[56] References Cited
UNITED STATES PATENTS

| | | | |
|---|---|---|---|
| 1,514,682 | 11/1924 | Wilson | 128/192 |
| 1,817,357 | 8/1931 | Fisher | 261/104 |
| 1,952,362 | 3/1934 | Bulger | 261/104 |
| 2,377,527 | 6/1945 | Siefken | 261/104 |
| 2,637,540 | 5/1953 | Rowe | 261/94 |
| 3,021,831 | 2/1962 | Byrge | 261/92 X |
| 3,043,573 | 7/1962 | Chandler | 261/99 X |
| 3,080,624 | 3/1963 | Weber | 261/142 X |
| 3,355,155 | 11/1967 | Heltzen et al. | 261/99 X |
| 3,659,604 | 5/1972 | Melville et al. | 261/DIG. 65 |
| 3,757,082 | 9/1973 | Goicoechea | 261/DIG. 65 |

Primary Examiner—Tim R. Miles
Assistant Examiner—Richard L. Chiesa
Attorney, Agent, or Firm—Dominik, Knechtel, Godula & Demeur

[57] ABSTRACT

An improved gas humidification system including a substantially closed chamber formed by a plurality of side walls, a bottom wall and a top wall having a gas inlet and outlet ports associated therewith, heat means associated with the bottom wall, and a humidification element removably positionable within the chamber comprising a heat conductive metallic member having an end for contact with the heat means and extending upwardly therefrom, and a layer of water absorbent material fixedly secured to at least one of the surfaces of the metallic member, the metallic member presenting a multi-faceted surface and the absorbent material paralleling the multi-faceted surface of the body portion of the metallic member thereby presenting an increase surface area for gas to pass over and around the humidification element at elevated temperatures thereby to increase the relative humidity of the gas prior to inhalation by a patient.

5 Claims, 10 Drawing Figures

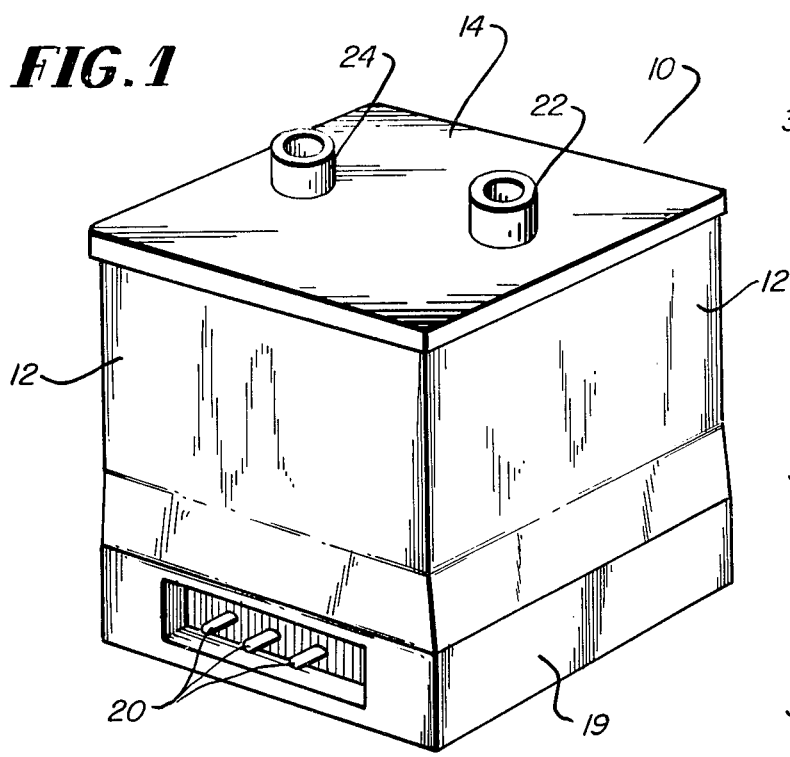
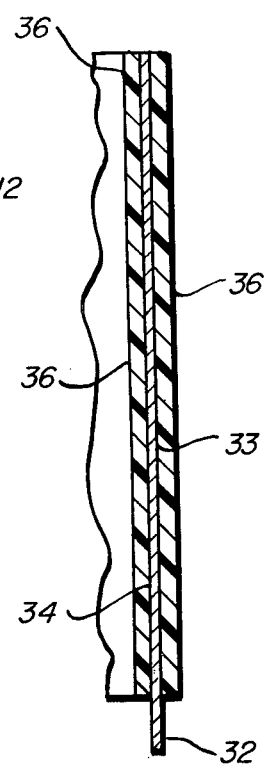
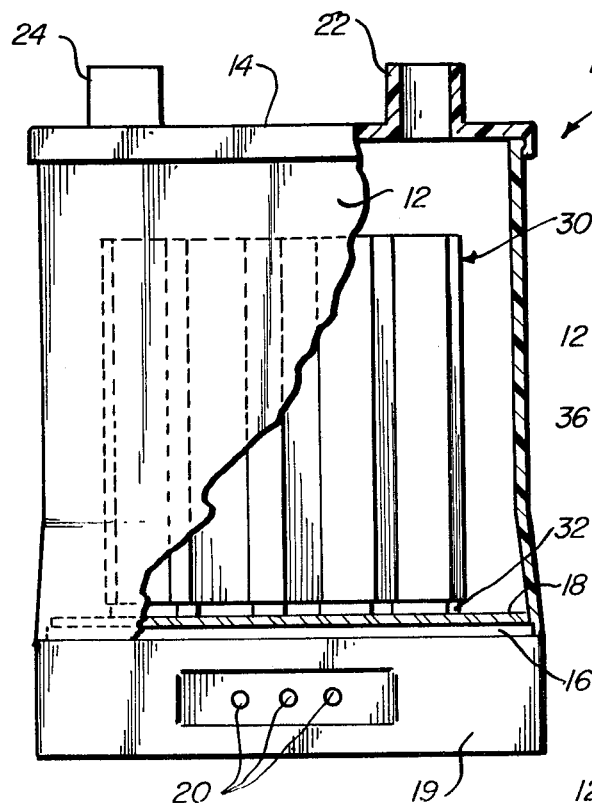
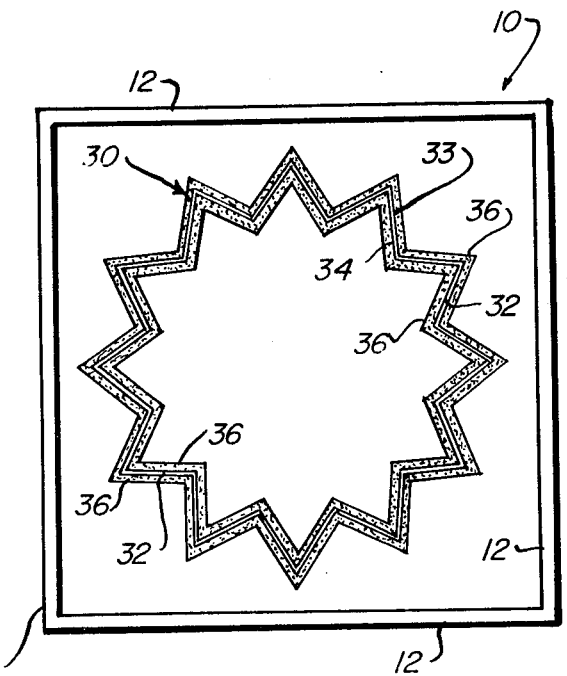

GAS HUMIDIFICATION SYSTEM

CROSS REFERENCE TO RELATED APPLICATION

This is a continuation of parent application Ser. No. 394,324, filed on Sept. 4, 1973, in the name of Walter I. Heath for GAS HUMIDIFICATION SYSTEM, now abandoned.

BACKGROUND OF THE INVENTION

It is well known in inhalation therapy that gases which are to be delivered to a subject or patient should be humidified prior to inhalation by the subject. Exemplary of the type of gases delivered to a patient will include oxygen as well as a mixture of air and oxygen which are generally mixed by an air entrainment device or system of the type generally employing a venturi tube and causing a pressurized mixing of the gases. This invention relates to an improved humidification system for accomplishing the humidification of gases delivered to a patient which system avoids many of the problems of various of the prior art units as well as permitting the further use of a gas entrainment system upstream of the humidification system.

One of the most common humidification systems involves the use of a chamber having a quantity of water therein, the chamber having a gas inlet port and a gas outlet port. Gas is delivered to the chamber through the inlet port and is bubbled through the water in order to raise the humidity of the gas afterwards which the gas is then directed to the gas outlet for delivery to the patient. And it is also accepted practice to incorporate a heater assembly with the chamber such that the water within the chamber is maintained at elevated temperatures in order to both heat and moisten the gases as the same passes through the chamber. One of the problems associated with the use of a gas bubbling system is that the bubbling of the gas through the water causes resistance and hence, in order to effectively operate the system, the gas must usually be pressurized in order to overcome the resistance encountered by the gas when entering and bubbling through the water. Where pressurizing of the gas is necessary, the possibility of utilizing an air or gas entrainment system upstream of the humidification system is magnified for the reason that in order to utilize an entrainment system of the venturi tube type, it is necessary to minimize the resistance of gas flow of the gases passing therethrough. It is therefore apparent that if the gas is to be pressurized prior to passing the same through the humidification system, it becomes very difficult if not impossible to also employ an air or gas entrainment system upstream from the humidification system. Furthermore, it is desirable to provide a humidification system which is more efficient and units heretofore known in the art which are also simplified in construction and permit ease of use.

Various other types of systems have been proposed for humidifying gases, generally for use in connection with respiratory care systems. For example, another humidification unit presently commercially available includes a chamber suitable for containing a quantity of water and wherein the bottom wall has a heater plate associated therewith. An aluminized insert element is provided which is formed of aluminum and constructed in the form of a spiral within the chamber. Between the concentric loops of the spiral there is positioned a sheet of absorbent paper in loose fitting relationship, the absorbent paper being manually fed into the spiral until the same is present between all of the concentric loops of the spiral. The aluminum element functions to conduct heat from the lower heater plate upwardly while the absorbent paper functions to take water up by capillary action thereby to provide moisture throughout the spiral assembly. A gas is inserted into the unit and must be specifically directed to the open end of the spiral with the necessity that the gas completely pass through the open concentric circles of the spiral and exit from the innermost portion of the spiral upwardly to a gas outlet and from there into an outlet tube for delivery to a subject. This unit is manufactured by the Fisher & Paykel Limited Company in Auckland, New Zealand and is distributed by OEM Medical Inc. of Edison, N.J. However, there would appear to be several drawbacks incident to the use of such a humidification device including the fact that the absorbent material must be manually wound into the spiral member by the operator. Hence, the absorbent material is not securely fixed to or bonded or laminated to the spiral aluminum member and this feature raises certain other difficulties. For example, the operator cannot adjust the physical distance or separation between the paper absorbent material and the concentric sides of the spiral member and hence there will be a variance in the spacing of the paper from the surface of the spiral member from one position to the next. The result is that as the gas flows through the spiral unit, a significant amount of resistance is met by the gas, and as the gas flow increases through the unit, the resistance will increase significantly. As has been previously indicated, when the resistance of the gas flow rate is increased, the possibility of utilizing an air entrainment device upline from the humidification system is greatly increased since in order to overcome the increase in resistance, it is necessary to pressurize the gas as it is delivered into the humidification unit. If the gas is pressurized prior to delivery to the humidification system, it becomes increasingly difficult if not impossible to utilize a venturi type entrainment device for mixing a quantity of oxygen with air upstream from the humidification system. Another drawback incident to the New Zealand unit resides in the fact that the gas must be directed into the spiral member along the outermost open edge in order that the gas pass through and around all of the loops of the spiral and exit from the immediate center of the spiral. Hence, it is necessary to establish a specific gas flow in order for the unit to function efficiently, and lacking such an air flow, the gas will not become efficiently humidified. Finally, it is to be noted that the manual insertion of the paper absorbent material within the spiral loop is a difficult operation consuming time thereby rendering the unit difficult to use and detracting from its overall commercial desirability.

Still another humidification unit which is described in the art relates to a temperature and humidity control unit developed by NASA and described in NASA TECH BRIEF Document No. B 72-10660. The unit described in this publication shows a temperature-humidity subsystem which is formed by a chamber suitable for carrying a quantity of water therein, the chamber being divided into three sub-chambers. The first chamber is adjacent the inflow line for the gas and contains a quantity of water therein and is in fluid communication with a reservoir for maintaining the water level in the lower chamber. The central chamber is formed by a pair of opposed perforated aluminum plates fixedly secured to a heater member which is in turn afixed to the bottom of the chamber. A plurality of gauze surgical sponge pads are packed into the second chamber extending from one of the perforated plates to the opposed perforated plate. The third chamber consists of the outflow chamber and is to the downstream side of the gauze surgical sponge. In point of fact, the unit was developed as a device for simulating exhaled human breath incident to various research work engaged in by NASA, however, it is believed that the device could similarly function as a humidification system for gas passed therethrough. The significant problem associated with the subject device, however, relates to the fact that it is flow-through type system in that the gas, in order to become humidified, must be passed through the first perforated plate, the gauze surgical sponge, and then through the opposed perforated plate before it exits the unit. Generally, the problems discussed above with other prior art units are similarly involved in the unit described herein in that as gas flows through the gauze surgical sponge, a significant amount of resistance is incurred and the resistance does increase as the gas flows through the surgical sponge. As indicated previously, when resistance is encountered and is increased during the operation of the humidification system, it is necessary to pressurize the gas in order to force the same through the unit. By pressurizing gases prior to delivery to the humidification system, it then becomes difficult if not impossible to employ gas entrainment devices upstream of the humidification system and this is generally regarded as a drawback in respiratory systems utilizing such humidification devices.

Another drawback of the unit described in the NASA TECH BRIEF is the fact that the perforated plates do not appear to conduct heat throughout the center chamber and hence, the gas passing through the gauze surgical sponge is not adequately humidified at elevated temperatures so that when the gas does reach the subject, the gas will not be efficiently humidifed. Furthermore, since heat is not conducted throughout the chamber area, it is quite obviously necessary to operate at higher temperatures in order to attempt to achieve some degree of elevated temperatures within the chamber in order to heat the gas as the same is being humidified. In addition, due to the structure of the unit, assuming that the two perforated plates do conduct heat, there will be a stratification of heat temperature throughout the chambers since the gas will be heated as it passes through the first perforated plate and cooled by evaporation as it passes through the gauze surgical sponge. When the gas finally reaches the opposed perforated plate, it will be once again heated and this heating-cooling-heating cycle causes a differential of heating of the gas and while the gas may be substantially humidified, the method of achieving such humidification is less efficient and greater amounts of heat are necessary.

Another further drawback incident to the device disclosed in the NASA TECH BRIEF is the fact that a water reservoir is provided for allegedly maintaining the water level in the three chambers below a constant level. However, due to the fact that the gases must be pressurized in order to force the same through the unit, the pressure will cause a variance of the water level in the reservoir and it is conceivable that the water level could rise with a resultant loss in efficiency, or the water level could lower to a point below the absorbent gauze surgical sponge after which there would be little to no humidification occuring since the sponges would no longer be wet and due to the lack of proper heat conduction by the perforated plates, there would be little heat in the chamber to vaporize what remaining water is in the chamber and cause vapor throughout the chamber. Hence, it is quite possible that the gas would not be humidified at all if the unit should run out of water or have the water level reduced to a level below the gauze surgical sponge.

Not withstanding the specific drawbacks of specific prior art units discussed above, generally, the prior art units are cumbersome in construction and rather expensive to manufacture. Furthermore, generally these units are difficult to set up and operate and hence, the amount of setup and operating time as well as cleanup time is a significant problem.

BRIEF SUMMARY OF INVENTION

This invention relates to an improved humidification assembly which comprises a chamber formed by a series of sidewalls, a bottom wall having a heater associated therewith and a top wall having a gas inlet and a gas outlet port positioned therethrough. The humidification element consists of a drop-in element formed by a metallic member having a generally vertical configuration with the lower end constructed for seatment on the bottom wall and having the body portion of the metallic member presenting a multi-faceted surface area. A layer of water absorbent material is fixedly secured to at least one of the opposed surfaces of the metallic member, the water absorbent material paralleling the multi-faceted surface area of the body portion of the metallic member and thereby greatly increasing the surface area over which the gas to be humidified may pass and take on humidity or moisture. In the preferred embodiment, the humidification element consists of the metallic member having the water absorbent material fixedly secured to both of the opposed surfaces of the metallic member and extending from a point spaced above the lower end of the metallic member upwardly to the very top of the metallic member. The metallic member generally functions to conduct heat from the heater or the heated water throughout the chamber while the water absorbent material fucntions to draw moisture throughout the absorbent material such that when the gas passes over and about the humidification element, the gas is heated to an elevated temperature and takes on moisture at such elevated temperatures.

It is therefore the principal object of this invention to provide a gas humidification assembly which is simplified in construction, efficient in operation, and minimizes the amount of setup, operation, and cleanup time involved in the use of such units.

Another object of this invention is to provide a humidification system for humidifying gases such as oxygen or the like, wherein the humidification element consists of a simple drop-in element which may be easily and simply positioned within the chamber after which the chamber may be closed and the unit is ready for operation.

Still a further object of this invention is to provide a humidification system of the type generally described above, wherein the chamber has a heat means associated with the same and the humidification element consists of a metallic member having one end designed for seatment on the heat means, and housing a body portion presenting a multi-faceted surface area, and a layer of water absorbent material fixedly secured to at least one of the surfaces of the metallic member and paralleling the multi-faceted surface thereof in order to present an increased surface area for gas humidification purposes.

In connection with the foregoing object, it is still another object of this invention to provide a humidification system wherein the humidification element includes a metallic member which is pleated in construction and presents a generally circular configuration and wherein the water absorbent material is fixedly secured to both opposed surfaces of the metallic member and extends from a point spaced upwardly from the lower portion of the metallic member upwardly to the very top end of the metallic member, the complete humidification element being freely positionable within the chamber and may be seated upon the heat means by positioning the lower end of the metallic member directly on the bottom wall incorporating the heat means therein.

Further features of the invention pertain to the particular arrangement of the elements and parts whereby the above-outlined and additional operating features thereof are attained.

The invention, both as to its organization and method of operation, together with further objects and advantages thereof, will best be understood by reference to the following specification, taken in connection with the accompanying drawings in which:

FIG. 1 is a perspective view showing the humidification assembly and specifically, the gas chamber;

FIG. 2 is a side-elevational view, partly in cross section, showing the construction of the gas chamber and the humidification element positioned therein, as well as the heat means associated with the chamber;

FIG. 5 is a side-elevational view in cross section showing the construction of the humidification element;

FIG. 6 is a top view showing the relative positioning of the humidification element wherein positioned within the chamber;

Figure 3:
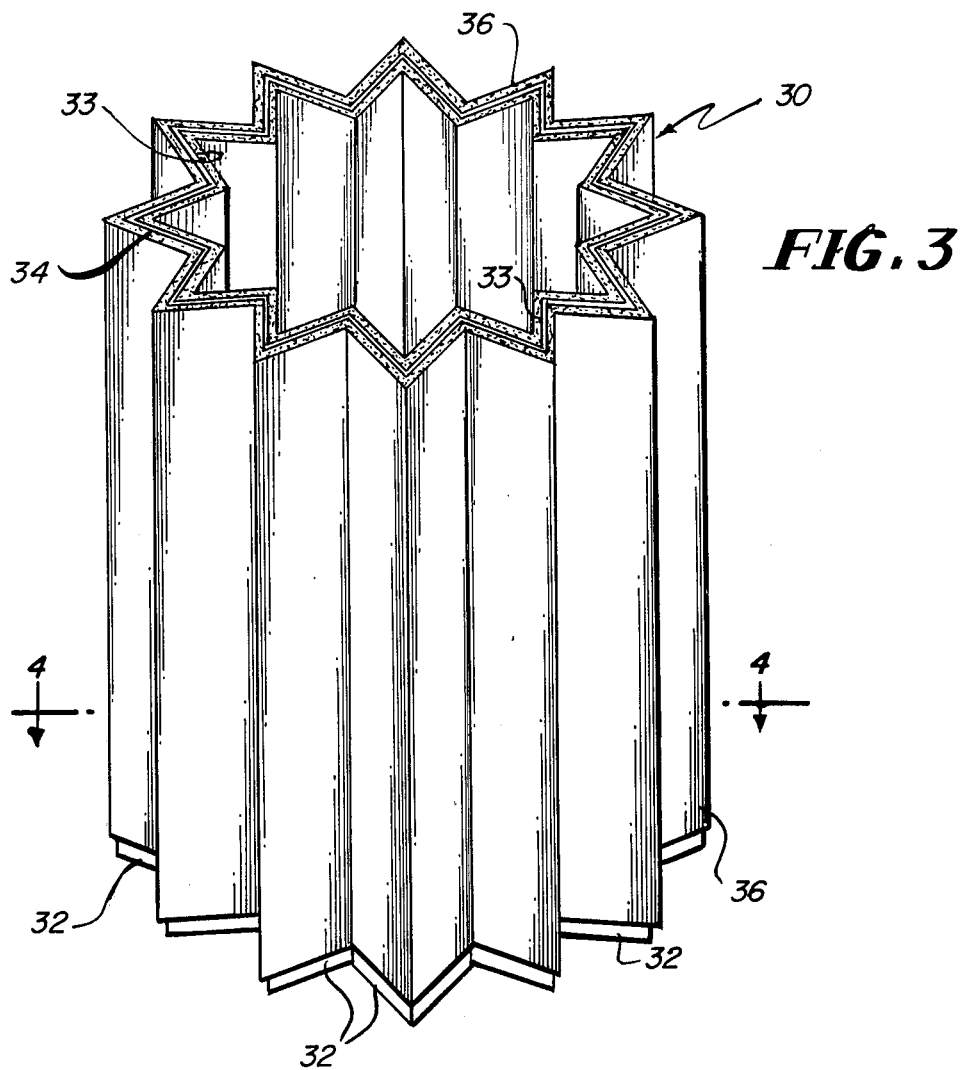
FIG. 3 is a side-elevational view showing the construction of the humidification elements.
Figure 4:
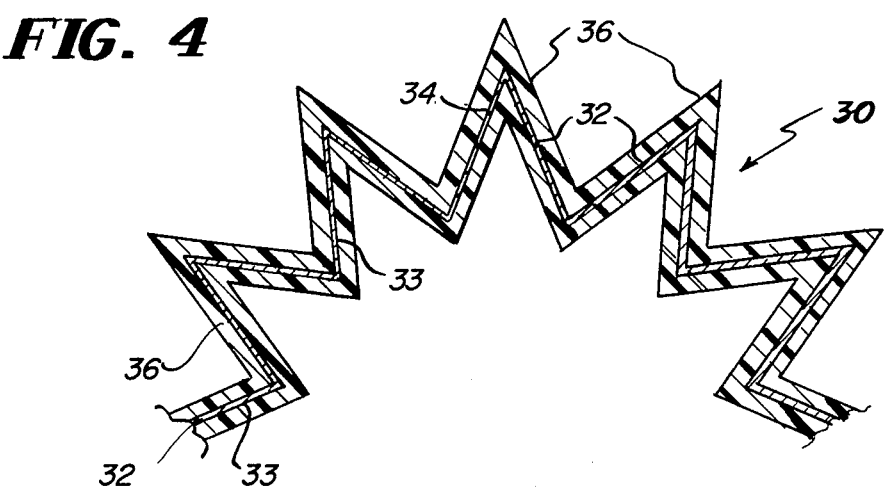
FIG. 4 is a cross-sectional view of the humidification element taken in the direction of the arrows along the line 4—4 of FIG. 3.

With reference to FIGS. 1 and 2 of the drawings, the novel humidifier 10 of the present invention is illustrated. The humidifier, generally referred to by the numeral 10, is formed by a plurality of side walls 12, a top wall 14, and a bottom wall 16. A heat plate 18 is disposed immediately above the bottom wall 16 and an electrical wiring chamber 19 is positioned immediately below the bottom wall 16, the electrical wiring chamber 19 accommodating the positioning of the circuitry incident to the heat plate 18 and having the heat plate connectors 20 extending outwardly therefrom. In use, the heating plate connectors 20 are interconnected with an appropriate outlet by means of an electrical cable of the type known in the art.

The top wall 14 is provided with a gas inlet port 22 and a gas outlet port 24 for the delivery and dispensing of gas into and out from the humidifier 10 respectively. However, the present invention, being a flow-by type system, permits the gas inlet and gas outlet ports to be positioned virtually anywhere in the chamber above the water level. In the preferred construction, the top wall 14 is completely removable from atop the side wall 12 and is engageable by means of a snap fit. It is contemplated that in the preferred embodiment, the humidifier chamber 10 is formed of a plasticized material such as nylon, Teflon, or the like.

The humidification element 30 represents the preferred embodiment contemplated by this invention and is illustrated in FIGS. 3 through 6 of the drawings. The humidification element 30 consists of a metallic member 32 which is formed of a heat conductive material such as aluminum. The metallic member 32 is shown to have opposed surfaces 33 and 34 respectively, each of the opposed surfaces 33 and 34 having a layer of absorbent material 36 fixedly secured thereto. It will be observed that the absorbent material 36 extends from the top portion of the metallic member 32 downwardly to a point spaced slightly upwardly from the lower end of the metallic member 32. This construction performs a function which will be more fully explained hereinafter.

As shown in FIGS. 3 through 6 of the drawings, in the preferred embodiment of the humidification element 30, the metallic member 32 is in the configuration of a pleated cylinder having the absorbent material 36 similarly paralleling the surface areas of the opposed surfaces 33 and 34 respectively.

Figure 9:
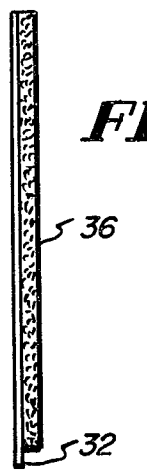
FIG. 9 is a side elevational view, in cross section, showing the details of construction of a humidification element having absorbent material fixedly secured to only one side of the metallic member.

In view of the fact that it is intended that the humidification system as proposed by this invention function as a flow-by or flow-over type system wherein the gas flows by the humidification element 30 and thereby is humidified, it is desirable to greatly increase the surface area over which the gas may pass in order to maximize the level of humidification of the gas. Hence, it has been found that the pleated cylindrical form operates quite efficiently to humidify the gas, especially where both of the opposed surfaces 33 and 34 respectively of the metallic member 32 are laminated with the absorbent material 36. However, as shown in FIG. 9 of the drawings, the humidification of the gas can be achieved where the metallic element 32 includes absorbent material 34 bonded to only one surface thereof and this construction is clearly contemplated in the scope of this invention.

As shown in FIGS. 1 and 2 of the drawings, the humidifier 10 includes a heat plate 18 adjacent the bottom wall 16 and in open communication with the interior of the humidifier chamber 10. The humidification element 30 may then be positioned within the humidifier chamber 10 by merely resting the lower surface of the metallic member 32 directly on the heat plate 18 as shown in FIG. 2 of the drawings. By having the lower portion of the absorbent material 35 spaced upwardly from the lower end of the metallic member 32, the absorbent material 36 is kept a safe distance away from the heat plate 18 to prevent any burning of the material 36. In addition, once the water level is lowered to a point immediately below the absorbent material 36, the rate of evaporation decreases significantly which, in turn, increases the time period over which the unit may continue to operate hence resulting in an additional safety feature.

The metallic member 32, being formed of a heat conductive material such as aluminum, functions to conduct heat generated by the heate plate 18 throughout the interior portion of the humidifier chamber 10 or at least conducts heat from the heated water through the chamber. Conducting of the heat throughout the interior portion of the humidifier chamber 10 facilitates evaporation and hence, maximizes a humidification of the gas. An additional important advantage obtained by having the metallic member 32 conduct the heat throughout the chamber is that the cooling effect brought about by the evaporation of water from the absorbent material 36 is greatly minimized. If the metallic member 32 were not present, the cooling effect brought about by water evaporation would tend to lower the temperature of the outgoing gas below the temperature of the ingoing gas. Hence, the presence of the metallic member 32 and its function of conducting heat throughout the chamber 10 is to ensure that cooling by evaporation is minimized and to ensure that the outgoing gas is at a higher temperature than the ingoing gas, assuming of course that the heat plate 18 is operating to provide heat. The abovedescribed function will occur even if no heat is provided by the heat plate 18, such as where the heat plate 18 is not connected by the operator, the metallic member 32 functioning to conduct whatever heat is available from the ambient conditions of the room throughout the chamber 10.

An additional function served by the metallic member 32 is to rigidify and support the absorbent material 36 such that the absorbent material 36 is permitted to stand vertically erect and thereby maximizing the surface area presented to the gases as they flow over and about the humidification element 30 for humidification purposes. In this manner, the gas passing through the humidifier 10 will be heated while also being humidified, and thereby having a greater relative humidity at the time that the gas exists from the chamber through the gas outlet port 24. Of course, as the gas passes through the delivery tube attached to the gas outlet port 24 and is delivered to the subject patient, the gas will cool somewhat and lose some of the moisture obtained in the humidifier 10. However, since the subject invention operates to maximize the humidification of the gas during passage through the humidifier 10, the slight loss of humidity during the time that the gas travels through the delivery tube to the patient will still result in the gas having a greater relative humidity when inhaled by the patient then with other units presently available.

It will be appreciated that by virtue of the construction of the humidification element 30, and the manner in which the same is positioned within the humidifier chamber 10, setup time of the humidifier 10 is greatly reduced since the operator need only manually insert the humidification element 30 into the chamber 10, and then close the top wall 14 by snap-fitting the same along the side walls 12. The delivery tubes are then attached to the gas inlet port 22 and gas outlet port 24 respectively, and the system is ready for operation. If and when the humidification element 30 becomes worn or is otherwise not suitable for use, it will be appreciated that the element 30 may be easily replaced with a minimum loss of time such that the humidification system may be kept in operation on a substantially continuous basis.

Insofar as the character of the absorbent material 36 is concerned, the profile for such a material is that it must be capable of tolerating heat and water emersion for substantial periods of time. It has been found that an epoxy-impregnated filter paper material will function quite efficiently for this purpose, as well as such material as cellulose foam and the like. Where cellulose foam is to be utilized humidification element 30 may be easily manufactured by dipping the metallic member 32 into the cellulose foam during the manufacturing procedure thereby laminating the same directly to the metallic member 32. It will be appreciated that if the manufacturing cost can be sufficiently reduced, the humidification element 30 can be made as a disposable element thereby further increasing the desirability of utilizing a humidifier 10 constructed in accordance with the present invention.

Where it is desirable to use a filter paper such as an epoxy-impregnated filter paper as the absorbent material, sheets of this material may be bonded to the metallic member 32 by nay heat and water resistant mastic, or by stitching the same directly to the metallic member 32. The particular means utilized for bonding or laminating or otherwise fixedly securing the absorbent material 36 to the metallic member 32 is a function of manufacturing time and cost, and limited only by the particular environment in which the humidification element 30 is utilized.

Figure 7:
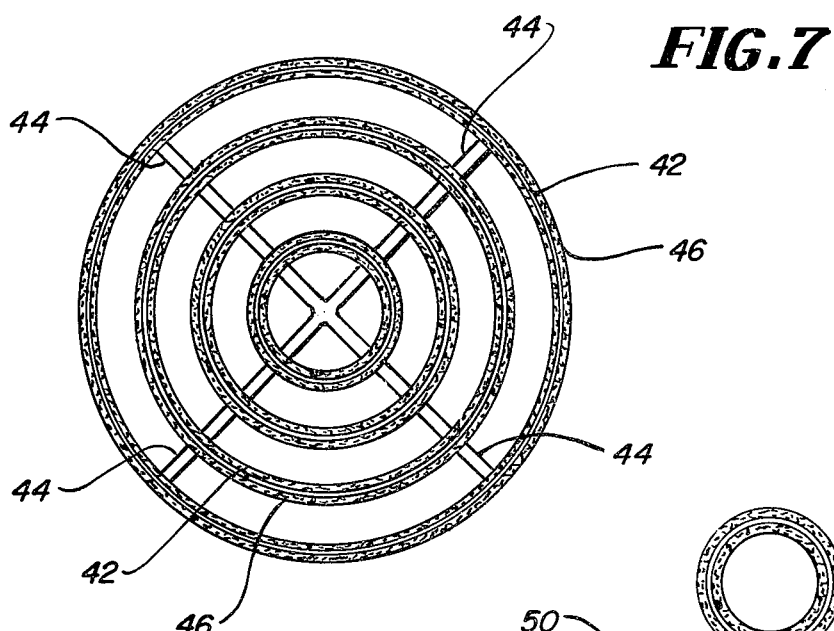
FIG. 7 is a top view showing the details of construction of another embodiment of the humidification element of the present invention.
Figure 8:
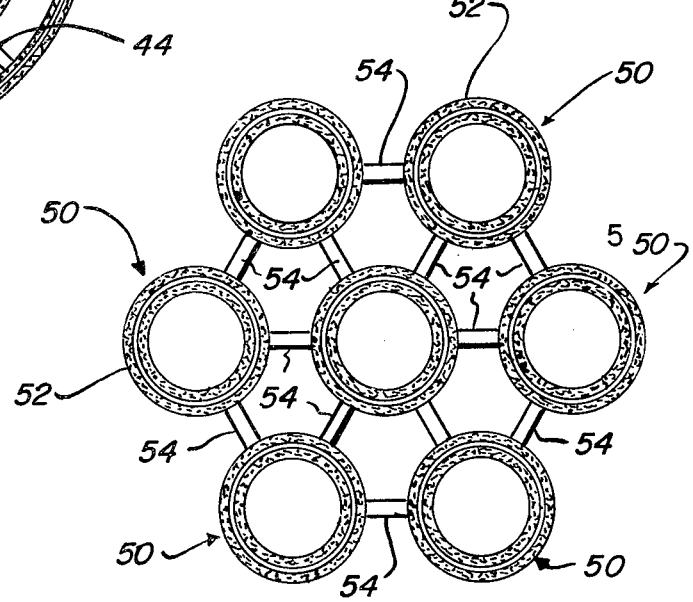
FIG. 8 is a top view showing the details of construction of still another embodiment of the humidification element embodied in the present invention.
Figure 10:
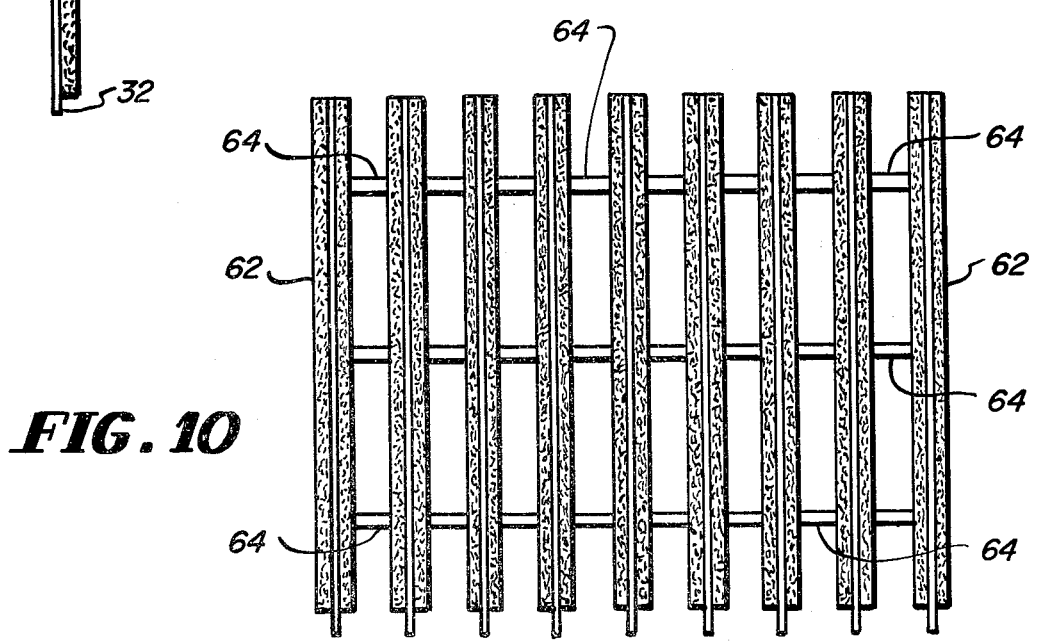
FIG. 10 is a top view showing the details of construction of still another embodiment of the humidification element embodied in the present invention.

As will be evident from FIGS. 7, 8, and 10 of the drawings, the humidification element may take a variety of forms and shapes. The main requirement is that any particular configuration utilized for the humidification element must maximize to the fullest the surface area exposed to the gases such that when the gases flow over and by the humidification element, the maximum degree of humidification is achieved. As shown in FIG. 7 of the drawings, the humidification element 40 shown therein may take the form of a series of concentric cylindrical members 42 which are held in fixed position by means of a plurality of braces 44. The absorbent material 46 is once again bonded or otherwise fixedly secured to each of the cylindrical members 42, and in the preferred embodiment, the absorbent material 46 is secured to both surfaces of each of the cylindrical members 42.

FIG. 8 illustrates still another embodiment humidification element 50 which is again, formed by a plurality of cylindrical members 52 held in fixed position relative to one another by means of plurality of braces 54. In the embodiment illustrated in both FIGS. 7 and 8 of the drawings, the overall sizing of the humidification elements 40 and 50 respectively is such that the same will easily fit within the humidifier chamber 10 or when the top wall 14 thereof is removed and the interior portion of the chamber 10 is exposed. Again, in each of these embodiments, a generally circular configuration is employed since such circular or cylindrical configuration expose a relatively high percentage of surface area in order to maximize the humidification of the gas as the gas passes over and about each of the humidification elements 40 and 50. In the embodiment as shown in FIG. 8 of the drawings, once again the absorbent material is bonded to each of the cylindrical members 52 in the manner heretofore described with regard to the other embodiments.

FIG. 10 of the drawings illustrates still another embodiment for a humidification element 60 which is formed in the configuration of a grid comprised of grid panels 62, the grid panels 62 being held in fixed relative position by means of support braces 64. Once again, each of the grid panels 62 is provided with the absorbent material fixedly secured to each of the opposed surfaces thereof in order to expose the maximum surface area to humidify the gases as it passes over, by, and through the grid panels 62.

Other configurations may easily be employed in order to achieve the same result such as polyhedron configurations, mesh or grid configurations wherein the metallic member would be formed from a metallic mesh or grid work and the absorbent material bonded thereto such as by dipping the metallic member in the cellulose foam during the manufacturing process, and a variety of other such configurations. As has been indicated heretofore, the principal consideration is to expose the maximum surface area in view of the fact that the present humidification system contemplates a flow-by or flow-over type system wherein the gases are heated and humidified by flowing over or by the humidification element.

It is clear that by virtue of the present invention, a humidification system is provided which minimizes the resistance generated by gas flow through the humidifier 10 and because of this fact, gas entrainment devices may be used upstream of the humidification system. For example, it is known to utilize air entrainment valves in order to obtain a mixture of oxygen and air prior to humidifying the mixture for delivery to a subject patent. For example, it is contempalted to utilize a mixing valve employing a controlled intake orifice venturi tube of the type described in co-pending application Ser. No. 205,204, filed on Dec. 6, 1971 and entitled FLUID MIXING VALVE filed in the name of Walter Heath and assigned to the assignee of the present invention. As has been indicated here and above other prior art type humidification systems do not permit the use of such air entrainment devices for the reason that the flow of gas through the humidification system generates a resistance because such units tend to be bubble-through or flow-through type systems and hence, it is necessary to pressurize the gas in order to pass the gas through the humidification system. The present invention avoids this problem by employing a flow-by or flow-over system and hence, virtually no resistance is generated during the passage of the gas through the humidifier. In view of this fact, it is not necessary to pressurize the gas prior to passing the same through the humidification system and therefore a venturi type air entrainment device may be used upstream of the humidification system.

Furthermore, in view of the fact that the metallic member 32 is employed for the purpose of conducting heat from the heat plate 18 throughout the chamber 10, the surface of the heater may be kept at a lower temperature than the heat required by other prior art units. For example, it is contemplated the subject invention can be operated with a temperature at the heat plate 18 at approximately 200° F and still obtain the necessary amount of heat throughout the chamber in order to heat the gas and cause evaporation of the water in order to humidify the gas. It is known that other prior art units must be operated at temperatures of as much as 400° F or higher in order to obtain the proper amount of heat since heat conduction is not generally employed in the same manner as contemplated by this invention. Another advantage obtained by the present invention is the fact that even if the water level should recede to a point below the absorbent material, since heat is conducted by the metallic member 32 throughout the humidifier chamber 10, the heat conduction will cause conduction of water vapor throughout the interior portion of the humidifier chamber 10 and therefore there will still be some level of humidification occurring. In addition, a certain amount of condensation occurs along the interior surfaces of the humidifier chamber 10 resulting in the water condensate dropping onto the humidification element 30 such that further humidification of the gas can occur. Therefore, the present invention provides a humidification system wherein humidification can occur even if very little water is left in the chamber due to the novel manner in which both heat and water vapor are conducted throughout the interior portion of the humidifier chamber 10.

It will also be appreciated that the humidification system provided by the present invention will achieve maximum humidification without at the same time requiring a specific gas flow pathway through the humidifier in the manner which is necessary in connection with some of the prior art units. The advantage thereby obtained is the fact that the chamber need not be specially constructed by having the gas inlet port 22 positioned in a specific location, but rather, may be positioned anywhere in either the side walls 12 or the top wall 14. There is also no attendant danger that the necessity for a specific flow pathway is not achieved thereby not humidifying the gas since the subject invention does not require any specialized gas flow pathway but only requires the gas be delivered to the interior portion of the humidifier chamber 10 in a manner to pass over or by the humidification element 30. In the preferred embodiment, the humidification element 30 consumes a greater portion of the interior of the humidifier chamber 10, and hence, when gas is delivered to the interior portion thereof, a fairly high level of humidification is assured.

It will therefore be appreciated that by virtue of the present invention, there has been provided an improved and efficient humidification assembly useful to humidify the gases at elevated temperatures prior to delivery to a subject patient. It will also be appreciated that the humidification system of the present invention is simplified in that the humidification system of the present invention is simplified in that the humidification element consists of a drop-in element which may be formed as a disposable unit and requires a minimum of setup time such that the humidification system overall may be operated on a substantially continuous basis. It will also be appreciated that the humidification element of the present invention operates by conducting heat and water vapor upwardly throughout the complete interior portion of the humidifier chamber such that maximum heating and humidification of the gas flowing therethrough is virtually assured. Furthermore, by contructing the humidification element as a unitary member with the absorbent material fixedly secured to the metallic member, no manual labor is required in order to position the absorbent material within the chamber. It is therefore appreciated that all of the above objects and advantages have been accomplished by means of the humidification system depicted herein in the various embodiments thereof to provide an extremely efficient and low-cost humidification system.

While there has been described what is at present considered to be the preferred embodiment of the invention, it will be understood that various modifications may be made therein and it is intended to cover in the appended claims all such modifications as followed in the true spirit and scope of the invention.

What is claimed is:

1. A device for humidifying gases used in connection with medical respiratory therapy, comprising in combination, a chamber formed by a plurality of side walls, a bottom wall, and a top wall, and having a gas inlet port and a gas outlet port associated with said chamber, said chamber having heat means associated with said bottom wall, said chamber being further constructed to receive and hold a quantity of water at a level above said heat means, a humidification element having an overall size to be easily positionable within said chamber, and further being freely removeable from said chamber, said humidification element comprising a heat conductive metallic member having one end thereof for removeably contacting said bottom wall and said heat means associated therewith, and extending upwardly therefrom and having the body portion thereof presenting a multi-faceted surface, said humidification element being constructed in the form of a convoluted body portion thereby presenting a multi-faceted surface area throughout the entire body portion, and a layer of water absorbent material fixedly secured to both of the opposed surfaces of the body portion of said metallic member and following the contours of said multi-faceted surfaces of said body portion such that said humidification element including said metallic member and water absorbent material covering, as a whole, is freely and easily removeable from said chamber while said humidification element provides both heat and moisture to gases passing thereacross, said absorbent material fixedly secured to said metallic member along both of the opposed surfaces thereof extends downwardly along said metallic member to a point spaced above the lower end of said metallic member such that the lower portion of said humidification element comprises an exposed peripheral skirt of said metallic member, whereby said humidification element may be inserted within said chamber having a quantity of water disposed therein, said metallic member functioning to conduct heat from said heat means upwardly throughout said chamber while said absorbent material absorbs water by capillary action to soak said absorbent materials such that gas entering said chamber through the gas inlet port passes along and over the multi-faceted humidification element to add elevated temperatures and is humidified prior to passage out through the gas outlet port.

2. The humidification device as set forth in claim 1 above, wherein said metallic member is formed from aluminum.

3. The humidification device as set forth in claim 1 above, wherein said absorbent material is formed from a material capable of tolerating heat and water emerging for substantial periods of time.

4. The humidification device as set forth in claim 3 above, wherein said absorbent material is formed from epoxy impregnated filter paper.

5. The humidification device as set forth in claim 3 above, wherein said absorbent material is formed from a cellulose foam.

* * * * *